United States Patent [19]
Kiyota et al.

[11] Patent Number: 5,698,853
[45] Date of Patent: Dec. 16, 1997

[54] INFRARED IMAGE PICKUP APPARATUS

[75] Inventors: Yasujiro Kiyota, Kawasaki; Naofumi Fushimi, Tokyo; Shigeru Kato, Kawasaki; Hideki Fujii, Tokyo, all of Japan

[73] Assignee: Nikon Corporation, Tokyo, Japan

[21] Appl. No.: 633,373

[22] Filed: Apr. 17, 1996

[30]     Foreign Application Priority Data

Apr. 18, 1995  [JP]  Japan .................................. 7-116311
Apr. 18, 1995  [JP]  Japan .................................. 7-116312

[51] Int. Cl.[6] ................................................ G01J 21/35
[52] U.S. Cl. ............................. 250/341.1; 250/338.5
[58] Field of Search ......................... 250/341.1, 338.5

[56]                 References Cited
              U.S. PATENT DOCUMENTS

| 4,490,613 | 12/1984 | Brame ........................... 250/341.8 |
| 4,496,839 | 1/1985 | Bernstein et al. .................. 250/341.6 |
| 5,076,699 | 12/1991 | Ryan et al. ........................ 356/437 |
| 5,523,569 | 6/1996 | Hornfeld et al. ................... 250/330 |

*Primary Examiner*—Constantine Hannaher
*Attorney, Agent, or Firm*—Shapiro and Shapiro

[57]            ABSTRACT

An infrared image pickup apparatus includes an infrared ray light source of the lamp bulb type radiating infrared rays including a particular absorption wavelength band in which an object to be detected absorbs light, toward a detection area around the object to be detected, a condensing optical system for condensing the infrared rays from the detection area, and an infrared ray detector for receiving the infrared rays condensed by the condensing optical system and converting them into an electrical signal.

8 Claims, 6 Drawing Sheets

INFRARED IMAGE PICKUP APPARATUS

BACKGROUND OF THE INVENTION

1. Field of the Invention

This invention relates to an infrared image pickup apparatus for detecting an infrared ray from an object and picking up the image of the object.

2. Related Background Art

As an infrared image pickup apparatus according to the prior art, there is known one provided with an infrared image pickup device 100 which, as shown, for example, in FIG. 17 of the accompanying drawings, detects the presence of any object (hereinafter referred to as the object to be detected) G and causes the detected object G to be visually displayed on a display screen. This infrared image pickup apparatus 100 is provided with a condensing optical system 101 for condensing an infrared ray, and an infrared ray detector (not shown) for receiving the infrared ray condensed by the condensing optical system 101 and converting it into an electrical signal. The infrared image pickup device 100 detects the object G to be detected on the basis of the difference in quantity of light between an infrared ray A not passing through the object G to be detected and an infrared ray B passing through the object G to be detected of the infrared rays incident on the infrared ray detector.

As a prior-art infrared image pickup apparatus provided with such an infrared image pickup device 100, there is a case where utilization is made of an infrared ray radiated from the background 102 or a case where a laser source 103 is used and use is made of a laser beam (infrared ray) of an infrared wavelength range radiated from the laser source 103. Also, the object G to be detected may be any one having an absorbing characteristic for the infrared area, and mention may be made, for example, of gases such as $CO_2$ and $H_2O$, high molecular compounds, paint, etc. The background 102 is, for example, a concrete wall or the like of a building which is behind the object G or with which the object G is partially in close contact. In the prior art that uses a ray radiated from the background, when the quantity of light of, the infrared ray radiated from the background 102 is small and therefore, the quantity in which this infrared ray is absorbed by the object G to be detected is also small. Thus, the difference in quantity of light between the infrared ray A and the infrared ray B is small. Accordingly, the object G to be detected cannot be reliably detected. Also when the quantity of the object G to be detected is small, the aforementioned difference in quantity of light becomes more minute, and this leads to the problem that the object G cannot be detected.

In the prior art, that uses a laser source the difference in quantity of light between the infrared ray A and the infrared ray B can be made great by the infrared ray from the laser source 103. However, the laser beam radiated from the laser source 103 has directionality and therefore, there is the problem that the irradiation area of the laser beam is narrow and the object G to be detected cannot be detected in a wide detection area. There is also the problem that the laser source itself is bulky and difficult to carry and consumes a great deal of electric power.

SUMMARY OF THE INVENTION

This invention has been made in view of such circumstances and a first object thereof is to provide an infrared image pickup apparatus which is capable of detecting an object to be detected reliably end in a wide detection area even when the quantity of the object to be detected is small, and which secures compactness, ease of carrying and low power consumption of a light source and yet is improved in detection sensitivity.

A second object of the present invention is to provide an infrared image pickup apparatus which can accurately detect an object to be detected even if there is no background such as a wall or a screen for radiating or reflecting an infrared ray behind the object to be detected.

To achieve at least the above-noted first object, the infrared image pickup apparatus of the present invention may comprise:

an infrared ray light source of the lamp bulb type radiating infrared rays including a particular absorption wavelength band in which an object to be detected absorbs light, toward a detection area around the object to be detected;

a condensing optical system for condensing the infrared rays from the detection area; and an infrared ray detector for receiving the infrared rays condensed by the condensing optical system and converting it into an electrical signal.

In the infrared image pickup apparatus of the present invention, the difference in quantity of light between an infrared ray not passing through the object to be detected and an infrared ray passing through the object to be detected can be sufficiently secured by a construction which has an infrared ray light source of the lamp bulb type radiating toward the detection area the infrared rays including the particular absorption wavelength band the object to be detected absorbs and in which the infrared ray detector receives the infrared rays from the infrared ray light source to thereby detect the object to be detected. Since the irradiation area of the infrared rays radiated from the infrared ray light source of the lamp bulb type is wide, the infrared rays are applied to a wide detection area. Also, even if the quantity of the infrared rays radiated from the infrared ray light source is increased to make the detection sensitivity of the object to be detected great, the light source itself will not become bulky like a laser source.

Also, an optical filter passing therethrough only the infrared rays of a particular absorption wavelength band is disposed on the light entrance side of the infrared ray detector, whereby the difference in quantity of light between an infrared ray not passing through the object to be detected and an infrared ray passing through the object to be detected can be made great.

To achieve at least the above-noted second object, the infrared image pickup apparatus of the present invention may comprises:

a condensing optical system for condensing an infrared ray;

an infrared ray detector for receiving the infrared ray condensed by the condensing optical system and converting it into an electrical signal;

an infrared ray light source radiating an infrared ray, of at least one of a plurality of absorption wavelength bands of an object to be detected, to the object to be detected; and an optical filter for passing only infrared rays of at least one of the plurality of absorption wavelength bands which differs from the absorption wavelength band radiated by the infrared ray light source, and causing them to be received by the detector.

In the above-described infrared image pickup apparatus, the infrared ray of at least one of the plurality of absorption wavelength bands the object to be detected absorbs is radiated from the infrared ray light source. When this infrared ray is applied to the object to be detected, the object to be detected absorbs the infrared ray. Thereafter, the object to be detected radiates infrared rays of the plurality of absorption wavelength bands. Of these infrared rays, light of an absorption wavelength band differing from that radiated by the infrared ray light source is detected by the infrared ray detector through the filter. Therefore, the object can be easily detected even in an environment wherein there is nothing behind the object to be detected.

DESCRIPTION OF THE PREFERRED EMBODIMENTS

A first embodiment of the present invention will hereinafter be described with reference to the drawings.

Figure 1:
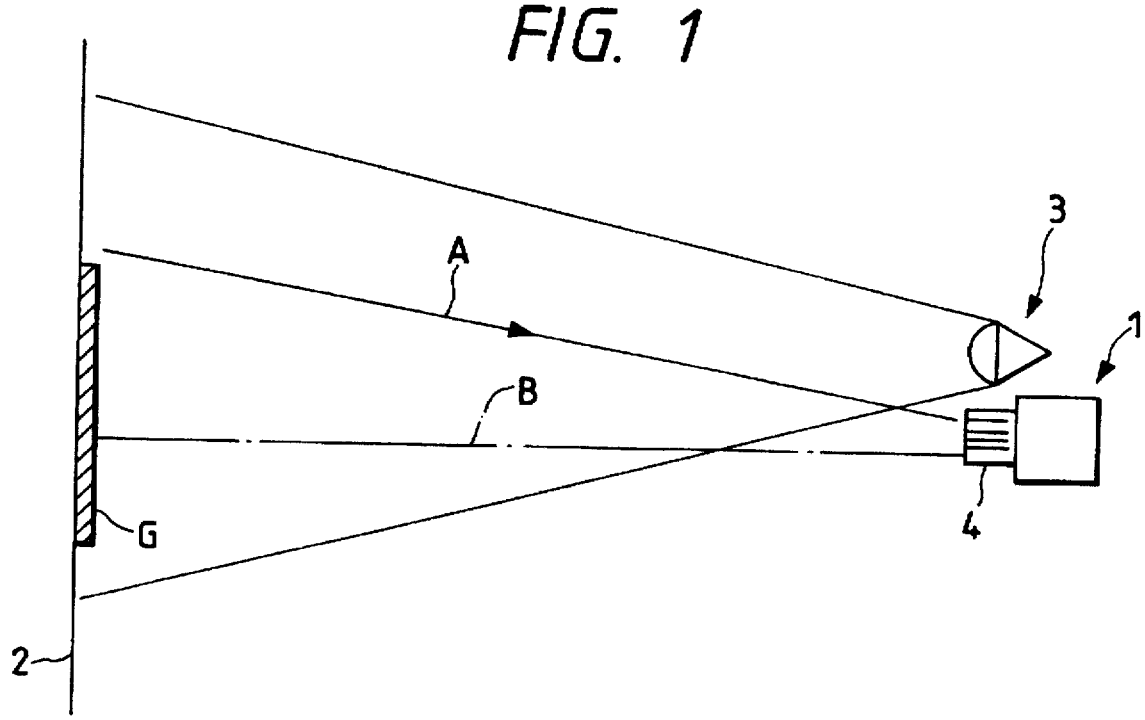
FIG. 1 shows an infrared image pickup apparatus according to a first embodiment of the present invention.

FIG. 1 shows the state of use of an infrared image pickup apparatus according to the first embodiment of the present invention. This infrared image pickup apparatus has an image pickup device 1, which detects the presence of paint which is an object to be detected and causes the detected paint G to be displayed on a display screen and visualizes it, and an infrared ray light source 3 which radiates infrared rays including a particular absorption wavelength band that the paint G absorbs toward a detection area in which there is a background 2.

Figure 2:
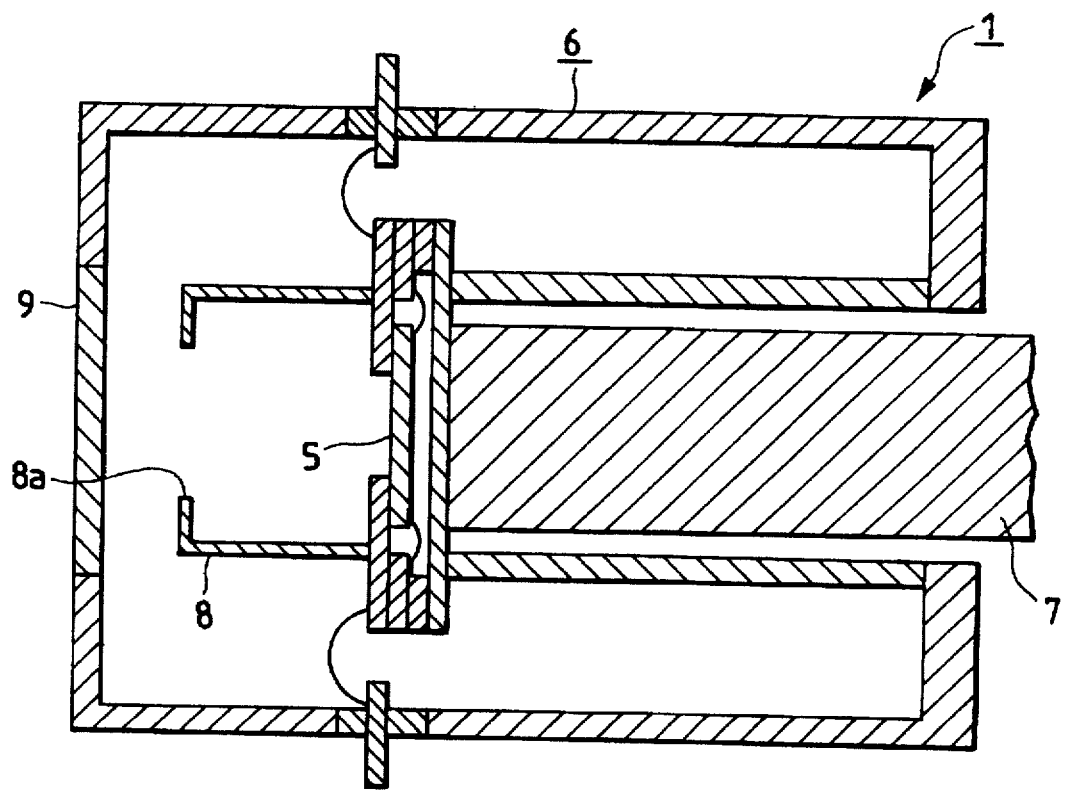
FIG. 2 is a cross-sectional view showing the principal portions of the infrared image pickup apparatus according to the first embodiment.

FIG. 2 is a cross-sectional view showing the principal portions of the infrared image pickup apparatus. The image pickup device 1, as shown in FIGS. 1 and 2, has a condensing optical system 4 for condensing the infrared rays, and an infrared ray detector (hereinafter simply referred to as the detector) 5 for receiving the infrared rays condensed by the condensing optical system 4 and converting them into an electrical signal. This image pickup device 1 further has a vacuum container 6 containing the detector 5 in vacuum and enveloped, a cooler 7 for cooling the detector 5 to a low temperature, and an aperture stop (cold shield) 8 for preventing any unnecessary infrared ray not passing through the condensing optical system 4 from entering the detector 5. The aperture stop 8 is disposed in the vacuum container 6 and is cooled to a low temperature by the cooler 7.

Figure 3:
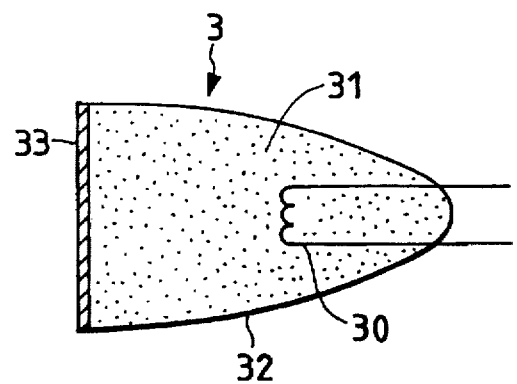
FIG. 3 is a cross-sectional view showing an infrared ray light source 3 of the lamp bulb type.

The infrared ray light source 3 of the lamp bulb type, as shown in FIG. 3, comprises a filament 30 which is a radiation source of electromagnetic wave, a reflector 32 forming a part of a hermetically sealed container enclosing a standard gas 31 therein and forwardly reflecting the electromagnetic wave radiated from the filament 30, and a plate-like outer shell member 33 forming a part of the hermetically sealed container with the reflector 32 and passing therethrough an electromagnetic wave of infrared ray wavelength range including a particular absorption wavelength band that the paint G absorbs. The filament 30 is made, for example, of tungsten wire.

Figure 4:
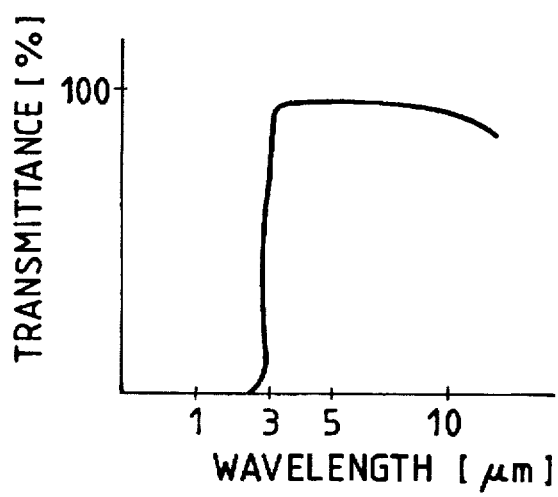
FIG. 4 is a graph showing the spectral transmittance characteristic of an outer shell member 33.
Figure 6:
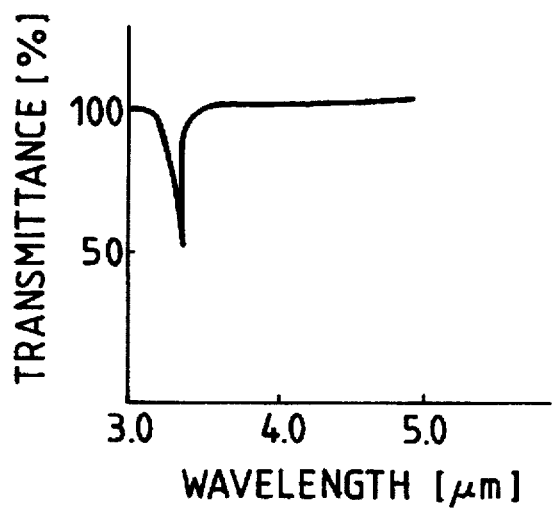
FIG. 6 is a graph showing the spectral transmittance characteristic of an object G to be detected.

The outer shell member 33 passes therethrough an electromagnetic wave of infrared ray wavelength range (infrared ray) including the particular absorption wavelength band (see the spectral transmittance characteristic of the paint G shown in FIG. 6) that the paint G absorbs. The spectral transmittance characteristic of the outer shell member 33 is shown in FIG. 4. This outer shell member 33 is formed, for example, of silicon (Si).

Figure 5:
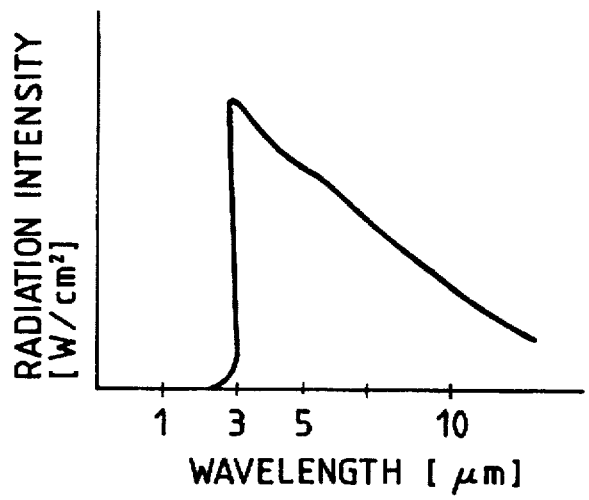
FIG. 5 is a graph showing the spectral radiation characteristic of the infrared ray light source 3.

The infrared ray light source 3 of the lamp bulb type having such a construction radiates infrared rays including the particular absorption wavelength band that the paint G absorbs toward the detection area in which there is the background 2. The spectral radiation characteristic of this infrared ray light source 3 of the lamp bulb type is shown in FIG. 5.

Figure 7:
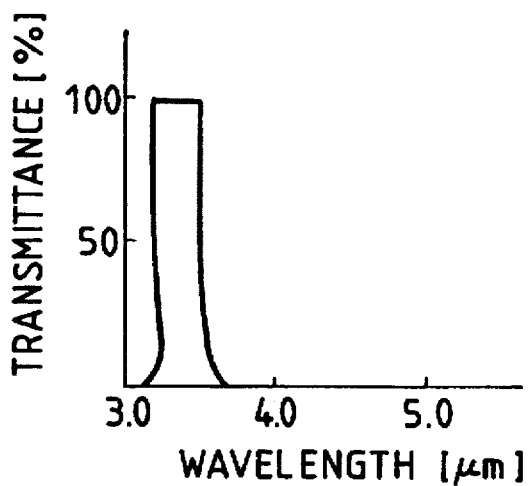
FIG. 7 is a graph showing the spectral transmittance characteristic of a filter 9 in the first embodiment.

In the vacuum container 6 of the image pickup device 1, a filter 9 forming a part of the vacuum container 6 is provided at a location opposed to the opening portion 8a of the aperture stop 8. This filter 9 passes therethrough only infrared rays of the particular absorption wavelength band included in the light radiated from the infrared ray light source 3. The spectral transmittance characteristic of this filter 9 is shown in FIG. 7.

When the infrared rays including the particular absorption wavelength band the paint G absorbs are radiated from the infrared ray light source 3 of the lamp bulb type toward the detection area in which there is the background 2, the radiated infrared rays are reflected by the wall 2. Of the infrared rays reflected by the wall 2, only an infrared ray of a particular absorption wavelength band passes through the filter 9 of the image pickup device and enters the detector 5.

The image pickup device 1 detects the presence of the paint G on the basis of the difference in quantity of light between an infrared ray A not passing through the paint G and an infrared ray B passing through the paint G, of the infrared rays entering the detector 5, and causes the detected paint G to visually displayed on a display screen, not shown.

According to the above-described first embodiment, 5 the apparatus has the infrared ray light source 3 of the lamp bulb type radiating the infrared rays including the particular absorption wavelength band toward the detection area in which there is the wall 2, and the detector 5 receives the infrared rays from the infrared ray light source 3 of the lamp bulb type to thereby detect the paint G. Therefore, a sufficient difference in quantity of light between the infrared ray A not passing through the paint G and the infrared ray B passing through the paint G is assured. Since the irradiation area of the infrared rays radiated from the infrared ray light source 3 of the lamp bulb type is wide, the infrared rays are applied to a wide detection area. Also, even if the amount of the infrared rays radiated from the infrared ray light source 3 of the lamp bulb type is increased to make the detection sensitivity for the paint G great, the light source itself does not become bulky as in the above-described laser source according to the prior art. Accordingly, even when the quantity of the paint is small, the paint can be detected reliably and in a wide detection area, and compactness, ease of carrying and low consumption of electric power of the light source itself are attained and yet the detection sensitivity can be improved.

Also, since of the infrared rays radiated from the infrared radiation light source 3 of the lamp bulb type, only the infrared ray of a particular absorption wavelength band passes through the filter 9 of the image pickup device 1 and is received by the detector 5, the detection sensitivity for the paint G is improved as compared with a case where the filter 9 is not provided. More particularly, assume that the quantity of light of an infrared ray A which does not pass through the paint G but enters the detector 5 when the filter 9 is absent is II (see FIG. 8), the quantity of light of the infrared ray A when the filter 9 is present is II' (see FIG. 8), the difference in quantity of light between the infrared ray A not passing through the paint G and the infrared ray B passing through the paint G is ΔI. Then the difference ΔI in quantity of light is equal when the filter 9 is present and when the filter 9 is absent. However, II'<II and therefore, the detection sensitivity ΔI /II' when the filter 9 is present is greater than the detection sensitivity ΔI/II when the filter 9 is absent. Accordingly, the paint G can be detected with high sensitivity.

Figure 8:
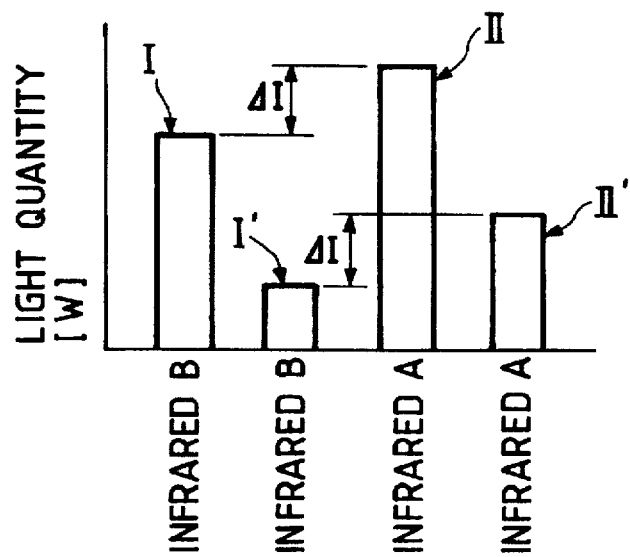
FIG. 8 is an illustration showing the quantity of light of an infrared ray received by an infrared ray detector 5.

In FIG. 8, the quantity of light of the infrared ray B passing through the paint G and entering the detector 5 when the filter 9 is absent as indicated by I, and the quantity of light of the infrared ray B passing through the paint G and entering the detector 5 when the filter 9 is present is indicated by I'. Accordingly, in this embodiment wherein the filter 9 is provided, the difference ΔI in quantity of light is represented by ΔI=II'-I'.

Figure 9:
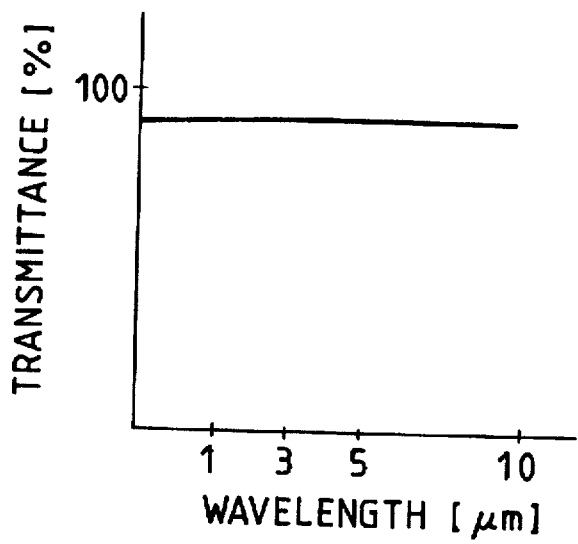
FIG. 9 is a graph showing the spectral transmittance characteristic of the outer shell member 33 formed of calcium fluoride ($CaF_2$)
Figure 10:
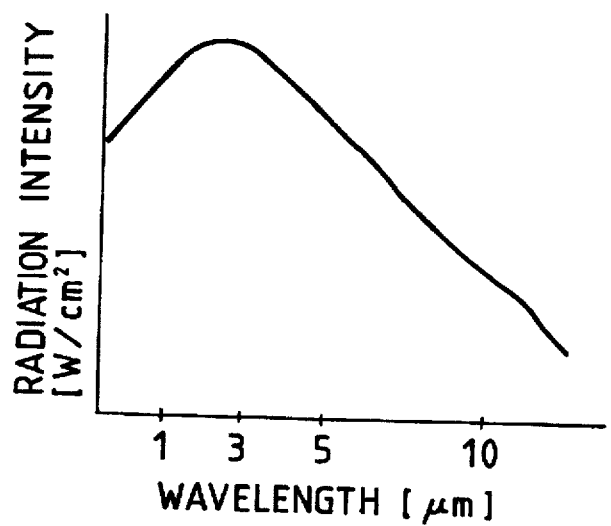
FIG. 10 is a graph showing the spectral radiation characteristic of the infrared ray light source of the lamp bulb type of which the outer shell member 33 is formed of calcium fluoride.

In the above-described first embodiment, the outer shell member 33 of the infrared radiation light source 3 of the lamp tube type may be formed of other material than silicon (Si), e.g. calcium fluoride (CaF₂). The spectral transmittance characteristic of the outer shell member 33 when it is formed of calcium fluoride (CaF₂) is shown in FIG. 9, and the spectral radiation characteristic of the infrared ray light source 3 of the lamp bulb type in that case is shown in FIG. 10.

Figure 11:
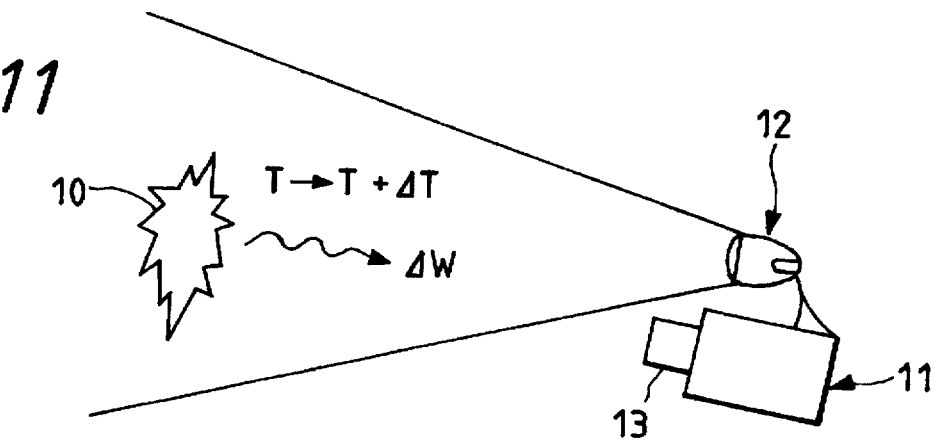
FIG. 11 shows an infrared image pickup apparatus according to a second embodiment of the present invention.

A second embodiment of the present invention will now be described. FIG. 11 shows an infrared image pickup apparatus according to the second embodiment. This infrared image pickup apparatus has an image pickup device 11 which detects the presence of an object 10 to be detected and causes the detected object 10 to be visually displayed on a display screen, and an infrared ray light source 12 which radiates infrared rays of a certain wavelength band.

The constructions of the principal portions of the image pickup device 11 are all the same as those in the first embodiment (with the exception that the kind of the filter 9 shown in FIG. 2 differs) and therefore need not be described in detail.

Figure 12:
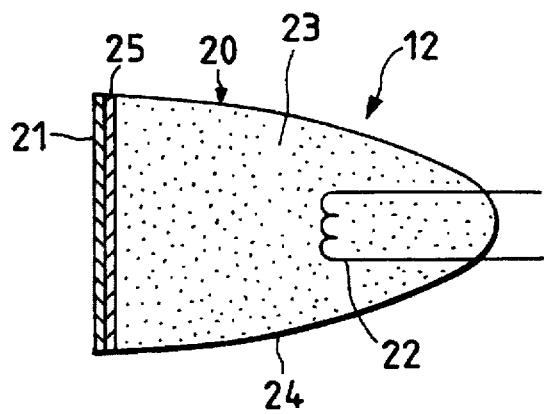
FIG. 12 is a cross-sectional view showing an infrared ray light source 12 of the lamp bulb type.

The infrared ray light source 12, as shown in FIG. 12, comprises an infrared ray light source 20 of the lamp bulb type and a filter 21 fixed to the front surface of the infrared ray light source 20. The infrared ray light source 20 of the lamp bulb type comprises a filament 22 which is a radiation source of electromagnetic wave, a reflector 24 forming a part of a hermetically sealed container enclosing a standard gas 23 therein and forwardly reflecting the electromagnetic wave radiated from the filament 22, and a plate-like outer shell member 25 forming a part of the hermetically sealed container with the reflector 24 and passing an electromagnetic wave of a certain infrared ray wavelength range therethrough. The filament 22 is made, for example, of tungsten wire.

Figure 14:
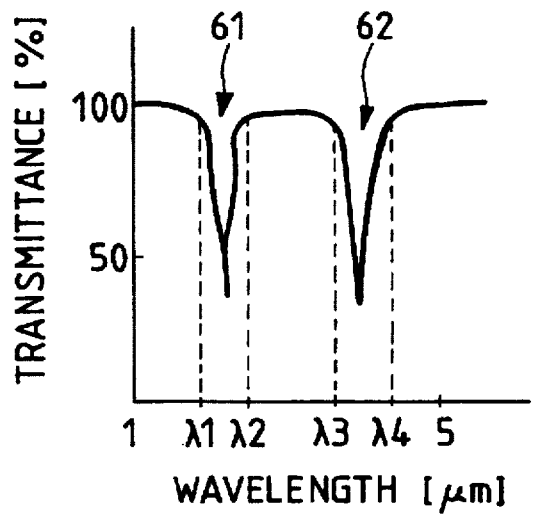
FIG. 14 is a graph showing the spectral transmittance characteristic of an object 10 to be detected.

The outer shell member 25 passes therethrough an electromagnetic wave of infrared ray wavelength range including a plurality of absorption wavelength bands (in this embodiment, two absorption wavelength bands 61 and 62 shown in FIG. 14) that the object G to be detected absorbs. The spectral transmittance characteristic of the outer shell member 25 is shown in FIG. 9. As is apparent from this figure, the outer shell member 25 passes therethrough an infrared ray of a wavelength band in the vicinity of 1 μm to 5 μm. The outer shell member 25 is formed of calcium fluoride (CaF₂).

Figure 13:
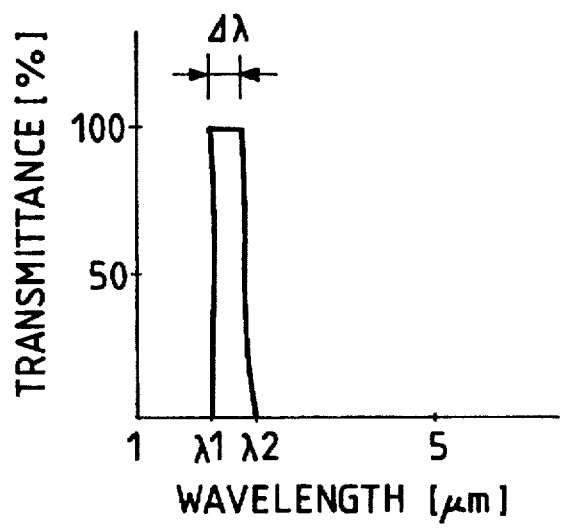
FIG. 13 is a graph showing the spectral transmittance characteristic of a filter 21.

The infrared ray light source 20 of the lamp bulb type having such a construction radiates an electromagnetic wave (infrared ray) of an infrared ray wavelength band in the vicinity of 1 μm to 5 μm including two absorption wavelength bands 61 and 62. The filter 21 is attached to the front surface of the outer shell member 25. This filter 21 passes the infrared ray of one absorption wavelength band 61 (hereinafter referred to as the first absorption band) of infrared rays of the two absorption wavelength bands 61 and 62 that the object 10 to be detected absorbs. The spectral transmittance characteristic of this filter 21 is shown in FIG. 13.

The infrared ray light source 12 having such a construction radiates an infrared ray of the first absorption band 61 (see FIG. 14).

Figure 15:
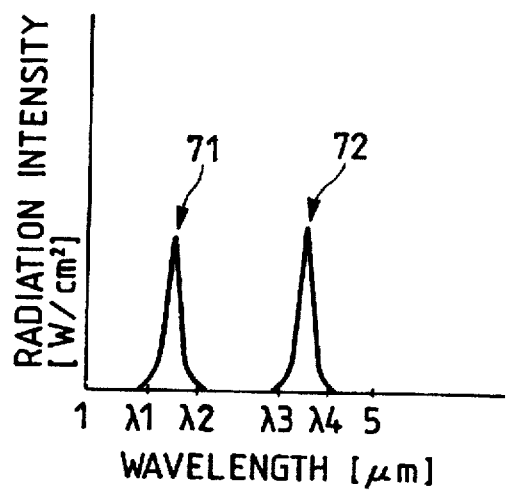
FIG. 15 is a graph showing the spectral radiation characteristic of the object 10 to be detected.
Figure 16:
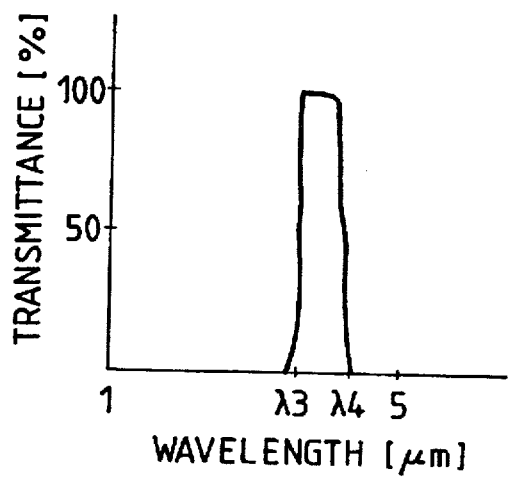
FIG. 16 is a graph showing the spectral transmittance characteristic of a filter 9 in the second embodiment.
Figure 17:
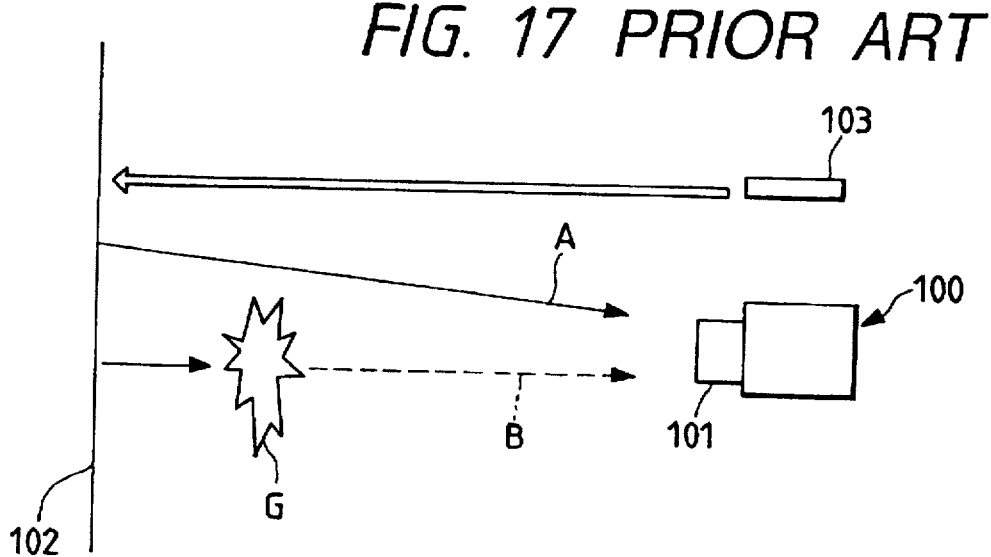
FIG. 17 is an illustration showing the state of use of an infrared image pickup apparatus according to the prior art.

The filter provided in the image pickup device 11 (the filter 9 shown in FIG. 2) passes therethrough only an infrared ray 72 radiated from the absorption wavelength band 62 (hereinafter referred to as the second absorption band) differing from the first absorption band 61, of infrared rays 71 and 72 (see FIG. 15 showing the spectral radiation characteristic of the object 10 to be detected) radiated from the object G to be detected when it receives the infrared ray of the first absorption band 61 radiated from the infrared ray light source 12. The spectral transmittance characteristic of this filter is shown in FIG. 16.

When the infrared ray of the first absorption band 61 (see FIG. 14) is applied from the infrared ray light source 20 of the lamp bulb type to the object G to be detected, the infrared ray of the first absorption band 61 is absorbed by the object G to be detected and by this absorption, the temperature of the object G to be detected rises by ΔT and therefore, the infrared rays 71 and 72 (see FIG. 15) are radiated from the two absorption bands 61 and 62 (see FIG. 14), respectively, that the object G to be detected absorbs. Of these infrared rays 71 and 72, only the infrared ray 72 radiated from the second absorption band 62 passes through the filter provided in the image pickup device 11 and enters the detector. That is, of the infrared rays 71 and 72 radiated from the object 10 to be detected, the infrared ray 71 radiated from the first absorption band 61 and the infrared ray radiated from the infrared ray light source 12 and not passing through the object G to be detected are intercepted by this filter. Accordingly, when the infrared ray light source 12 applies the infrared ray to the object 10 to be detected, energy ΔW radiated from the object to be detected is detected and the detected object 10 can be visually displayed on a display screen, not shown. Also, the detection sensitivity for the object 10 to be detected is not affected by the amount of infrared ray radiated from the infrared ray light source 12, and high detection sensitivity is obtained.

In the above-described second embodiment, the outer shell member 25 of the infrared ray light source 20 of the lamp bulb type may be formed of silicon (Si).

Also, in the above-described second embodiment, when for example, there are three or more absorption wavelength bands that object 10 to be detected absorbs, the infrared ray light source 12 can radiate an infrared ray of at least one of those absorption wavelength bands. Also, as previously described, as the object to be detected in the present embodiment, mention may be made of a gas such as $CO_2$ or $H_2O$, a high molecular compound or the like, and they can be viewed.

What is claimed is:

1. An infrared image pickup device for detecting an object which has first and second infrared absorption wavelength bands, comprising:

an infrared light source of the lamp bulb type for radiating infrared light of the first absorption wavelength band toward a detection area around said object; and an infrared image pickup device to provide an image of said object based on infrared light only of the second absorption wavelength band from said object, said infrared image pickup device having a condensing optical system for condensing infrared light from the object, an infrared light detector for receiving infrared light condensed by said condensing optical system, and an optical filter for passing infrared light only of the second absorption wavelength band and disposed to pass infrared light of the second absorption wavelength band from the object to said detector and to prevent infrared light of the first absorption wavelength band from the object from reaching said detector.

2. An apparatus according to claim 1, wherein said infrared light source has a filament which is a radiation source of electromagnetic waves, a hermetically sealed container hermetically enclosing said filament therein, and an outer shell member forming at least a part of said hermetically sealed container and transmitting infrared light of the first absorption wavelength band.

3. An apparatus according to claim 2, wherein said outer shell member is formed of silicon.

4. An infrared image pickup apparatus for detecting an object which has a plurality of infrared absorption wavelength bands, comprising:

an infrared light source of the lamp bulb type for radiating infrared light of a first of said absorption wavelength bands toward a detection area around said object; and an infrared image pickup device to provide an image of said object based on infrared light only from at least one of said absorption wavelength bands other than said first absorption wavelength band, said infrared image pickup device having an optical filter device for passing infrared light only from the at least one of said absorption wavelength bands other than said first band, and an infrared detecting device disposed for detecting the infrared light from said object passed through said optical filter device.

5. An apparatus according to claim 4, wherein said infrared light source has a filament which is a radiation source of electromagnetic waves, a hermetically sealed container hermetically enclosing said filament therein, and an outer shell member forming at least a part of said hermetically sealed container and transmitting infrared light of the first absorption wavelength band.

6. An apparatus according to claim 5, wherein said outer shell member is formed of silicon.

7. An infrared image pickup method for detecting an object which has first and second infrared absorption wavelength bands, comprising:

radiating infrared light of the first absorption wavelength band from a lamp bulb type infrared light source toward a detection area around said object;

passing infrared light from said object to an infrared detector of an infrared image pickup device through an optical filter which passes infrared light only of the second absorption wavelength band; and producing an image of said object based only on the light received by said detector via said optical filter.

8. An infrared image pickup method for detecting an object which has a plurality of infrared absorption wavelength bands, comprising:

radiating infrared light of a first of said absorption wavelength bands from a lamp bulb type infrared light source toward a detection area around said object; and passing infrared light from said object to an infrared detecting device of an infrared image pickup device through an optical filter device which passes infrared light only from at least one of said absorption wavelength bands other than said first absorption wavelength band; and producing an image of said object based only on the light received by said detecting device via said optical filter device.

* * * * *